United States Patent [19]
Borzemsky

[11] Patent Number: 5,387,059
[45] Date of Patent: Feb. 7, 1995

[54] DRILL BIT WITH IMPROVED STABILITY

[76] Inventor: George E. Borzemsky, 211 Oakdene Ave., Teaneck, N.J. 07666

[21] Appl. No.: 110,967

[22] Filed: Aug. 24, 1993

[51] Int. Cl.⁶ .................... B23B 51/02; A61C 3/02
[52] U.S. Cl. .................... 408/226; 408/230; 433/165
[58] Field of Search .............. 408/226, 230, 715, 229, 408/83, 229; 433/165; 606/80

[56] References Cited

U.S. PATENT DOCUMENTS

| | | | |
|---|---|---|---|
| 2,897,695 | 8/1959 | Winslow | 408/715 X |
| 4,345,899 | 8/1982 | Vlock | 433/165 |
| 4,968,193 | 11/1990 | Chaconas et al. | 408/225 X |

FOREIGN PATENT DOCUMENTS 90214 7/1980 Japan .................... 408/230

OTHER PUBLICATIONS

Advertisement For Brasseler Drill, *Dental Products Report*, May, 1994.

*Primary Examiner*—Steven C. Bishop
*Attorney, Agent, or Firm*—Arthur J. Plantamura

[57] ABSTRACT

A modified flute drill which prevents non-circular oval shaped drill holes which occur from incidental lateral or non-axial forces imparted by the operator is provided. The design modification is based on relieving, beveling, or dulling of the leading or side-cutting edge of the flutes of the drill bit for most of the length of the drill bit except for an initial specified length of the flutes where the leading edge of the flutes retains its sharpness and side-cutting capacity. The flute modification additionally imparts to the fluted drill a capacity of self-directional stability after the drill begins its penetration into the material being drilled, at the chosen initial angle of orientation of the drill bit, due to the absence of a side-cutting edge on the following major portion of the drill flutes.

4 Claims, 2 Drawing Sheets

DRILL BIT WITH IMPROVED STABILITY

The invention relates to an improved fluted drill bit and more particularly, to a superior functioning fluted drill bit that minimizes ovaling of the drilled hole due to any inadvertantly imparted lateral or non-axial forces when the drill bit is in use.

BACKGROUND OF THE INVENTION

Prior art fluted drill bits are designed to remove drilled material that is formed as the drill bit penetrates the material being drilled. Such bits have a sharp leading edge along the entire length of the flutes. Such bits may have one, two, three or more flutes. As a consequence of the sharp leading edge along the entire length of the flutes, the bit has a side-cutting ability which also extends the entire length of the flute, and if lateral or non-axial forces are imparted to the drill bit during drilling, this results in a non-circular widened or oval shaped hole as the drilled hole deepens, during manual or hand-held drilling. The developing of a widened or oval shape to the drilled hole is caused by the sharp leading edge along the entire length of the flutes, when the drill bit is being used to drill a hole, especially when used in manually drilling.

The departure from a true circular hole, i.e., the tendency to a widening or oval shaping of the hole results in a defininte disadvantage for applications that require a perfectly circular cylindrical hole such as is most important in bone surgery, especially in the mouth where drilling access is limited.

Accordingly, a need exists for a drill bit which avoids the cutting potential that is present from the leading cutting edges of almost the whole length of the flutes such as occurs with prior art drill bits; and that the side cutting capacity of the flutes of the drill bit be limited to an initial minimal length portion of the flutes of the drill bit.

SUMMARY OF THE INVENTION

It is a primary object of the invention to provide a novel fluted drill bit having improved hole drilling accuracy.

It is a more particular object of the invention to provide a fluted drill bit in which the side cutting edges of the flutes of the drill, for most of the length of the drill bit, except for an initial specified length portion of the flutes of the drill, where the leading edge of the flutes of the drill bit, are relieved to form a non-cutting edge.

It is another object of the invention to provide a novel drill bit with a side cutting capacity limited to a specified length portion of the leading edge of the flutes of the drill bit near the tip of the drill bit.

A further object of the invention resides in providing a fluted drill bit in which the side cutting edge of most of the length of the flutes, beyond an initial length portion of the flutes at the tip or point of the drill bit, is relieved of a side cutting capability, and where the outer surface of the flutes, for the entire length of the flutes has a constant non-changing diameter (portion no. 19 of FIG. 1) and provides a drill guiding capability only, avoiding a side cutting potential of the formed hole.

It is another object of the invention to provide a fluted drill bit for hand drilling operations which minimizes the drilling of non-circular holes caused by lateral or non-axial forces that are incidentally imposed during drilling operations.

Additional features and advantages of the invention will become apparent from the detailed description and drawing and from the claims.

DETAILED DESCRIPTION OF THE PREFERRED EMBODIMENT OF THE INVENTION

The drill bit of the invention comprises a modified flute drill which prevents non-circular oval shaped drill holes which occur from incidental lateral or non-axial forces imparted by the operator. The design modification is based on relieving, beveling, or dulling of the leading or side-cutting edge of the flutes of the drill bit for most of the length of the drill bit except for an initial specified length of the flutes, where the leading edge of the flutes retain their sharpness and side cutting capacity. The flute modification additionally imparts to the fluted drill a capacity of self-directional stability after the drill begins its penetration into the material being drilled at the chosen initial direction, i.e., the initial angle of orientation of the drill to the material being drilled.

Figure 1:
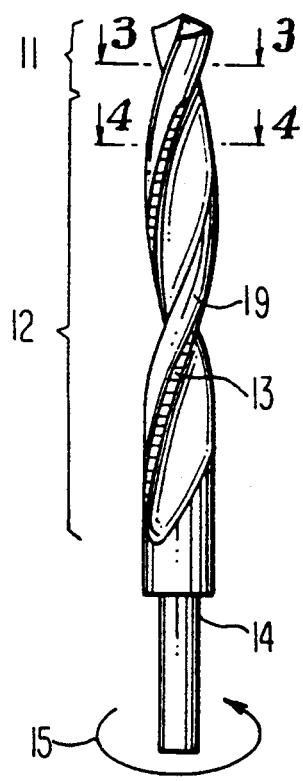
FIG. 1 is a side elevation of a drill bit according to the present invention.

Referring to the drawing, FIG. 1 shows a drill configuration according to the invention and comprising for illustration a two-flute drill bit. As shown in FIG. 1, the drill bit comprises a fluted portion which comprises most of the length of the drill bit and is referenced as bracketed segments 11 and 12 and a shank portion 14 of reduced diameter which is inserted into the chuck of a conventional drill tool.

As shown in the drawing, the cross-sectional view of the drill flutes at the first segment 11 (FIG. 1) of the total length of the drill flutes is provided with a sharp leading or side-cutting edge. The remainder of the fluted segments, a portion 12 comprises flutes having a bevel modification of the leading or side-cutting edge. In other words, the leading edge of the flutes of the portion which extends beyond the initial minimal specified length of the flutes i.e. portion 11, is relieved of side-cutting capability. As the drill bit increases in penetration of the material being drilled, the resistance to lateral or non-axial haphazardly or incidentally induced forces during drilling increases. The deeper the drill enters the material being drilled, the greater is the self-directional stability gained as the beveled leading edges of the flutes of the drill bear on the sides of the drilled holes without cutting of the sides of the hole being drilled.

With respect to the reference numerals indicated in FIG. 1, numeral 13 refers to the leading edge of the flutes which have been beveled, arrow 15 indicates the direction of rotation of the drill, and numeral 19 refers to the outer surface of the flute which contacts or bears against the wall of the hole being drilled. Surface 19 is also referred to as the drill-to-bore-wall-contacting surface of the drill bit.

Figure 2:
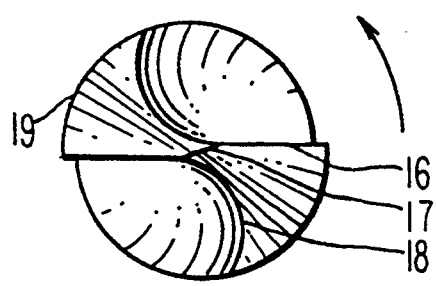
FIG. 2 is a front end view of the drill bit.

Referring to FIG. 2, numeral 17 refers to the center point of the tip of the drill bit, 16 refers to the end drill point leading (cutting) edge of the drill bit, with trailing portions shown at 18.

Figure 3:
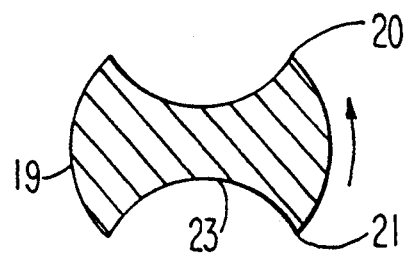
FIG. 3 is a sectional view taken along line 3—3 in FIG. 1.

Referring to FIG. 3, the leading or side-cutting edge 20, and the trailing edge 21 of the flute in the side-cutting portion of the flutes are shown in cross section, with the grooves 23 of the drill bit.

Figure 4:
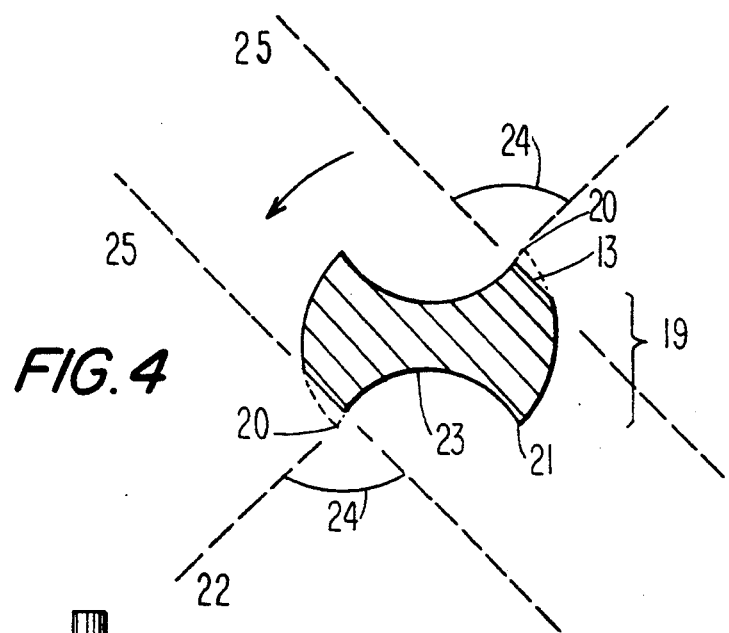
FIG. 4 is a cross-sectional view taken along line 4—4 in FIG. 1.

Referring to FIG. 4, this is a cross section through the bracketed portion 12 of FIG. 1. This portion of the flutes, which follows the portion 11, functions solely as a non-side-cutting guide portion to maintain the directional alignment of the drill, as the hole is being drilled. This non-side-cutting portion 12, is effected by a relieving or beveling of the leading or side-cutting edge of the flute, and the beveling is shown as a broken line 25. The angle of orientation of the beveling line 25 is shown as forming a 90 degree angle with a broken line 22 which goes from the center of the diameter of the drill and extends to the original leading edges of the flutes. The depth of the beveling, line 25, is shown to be at 5 percent of the diameter of the drill.

Figure 5:
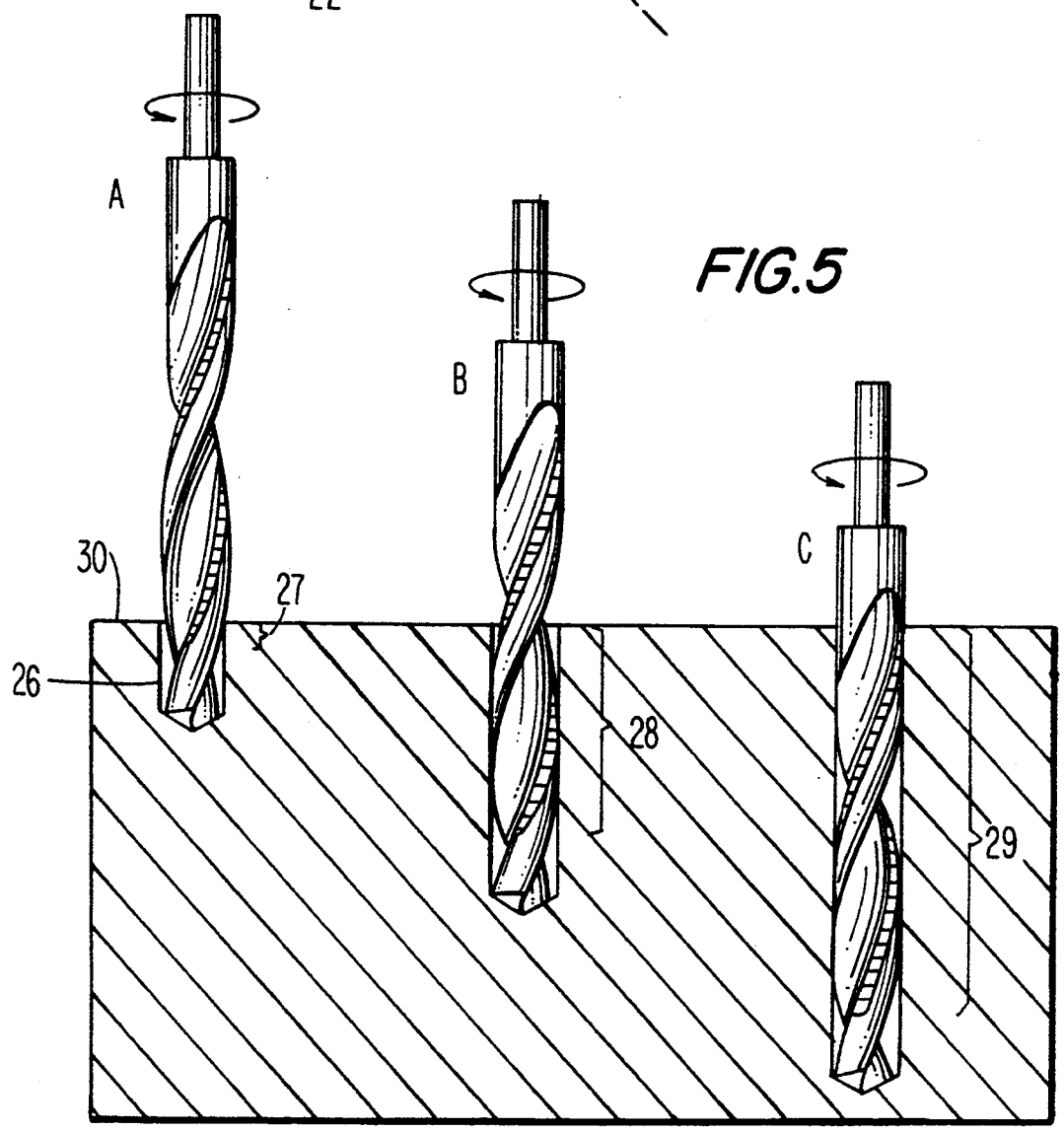
FIG. 5 is a side elevational view illustrating the drill bit in a material being drilled at three different depths of drill penetration into the material.

Referring to FIG. 5, the wall of the bored hole as formed as shown at 26, with region 27 of sequence (A) of the drill bit indicating the flute guide portion which has entered the material 30 being drilled. This bracketed region 27 of the drill bit is just beginning to exert its guidance effect, resisting of any incidental laterally induced forces. As the drill bit extends its penetration, shown at sequence (B) of FIG. 5, the bracketed region 28 of the drill bit, which is guiding the drill bit, and is substantially extended; this greater depth provides correspondingly greater self-directional stability action. As the penetration is extended further, shown as segment (C) of FIG. 5, and as shown as the extended guide portion 29, provides a substantial lateral force resistance tending to maintain alignment of the drill bit without cutting against the wall of the hole bored. The material 30 which is drilled, may comprise any suitable composition, however, the invention provides its most advantageous effect where the material being drilled is relatively likely to lend itself to a distortion by side cutting on the wall, such as bone, tooth dentin, and the like.

It is thus seen that with the drill bit of the invention, which limits cutting by the flute edges to only a relatively small part of the initial end of the drill bit, it is possible to drill a perfectly circular, cylindrical hole. Due to the elimination of side cutting edge surfaces at the upper part 12 of the flutes, incidentally occurring lateral or non-axial forces that are induced inadvertently by instability or misalignment of the operator's hands, will not interfere with or alter the shape of an initially formed precise hole. This formation of a precise, i.e., non-distorted hole, is important in bone surgery and especially bone surgery in the mouth where accuracy is important and drilling access is very limited. The formation of an accurately perfectly formed hole is also critical in situations involving less dense, medullary bone wherein an oval shaped, non-circular hole can occur relatively easily and interferes with a solid grip necessary for the desired result.

It is important to note that the improved drill of the invention does not entirely eliminate the side cutting capacity of the flutes, but rather, limits the side cutting capacity of the flutes to a relatively short portion of the leading edge of the flutes near the point of the drill bit as illustrated by a portion 11 of FIG. 1. The remaining "modified" region of the flutes, which extends over most of the length of the drill bit, and which is illustrated as bracketed portion 12 in FIG. 1, is devoid of side cutting capacity and instead functions solely in a drill bit guiding capacity. Accordingly, once the hole is begun, as effected by a portion 11 of the drill bit as shown in FIG. 1, and the modified or beveled portion of the flutes as shown by portion 12 of FIG. 1 begin to enter the deepening hole, the drill bit of the invention maintains the initial direction of the drilling by resisting any lateral, non-axial forces imparted by an operator's hands and without destroying the perfect circular symmetry of the initially drilled hole, because portion 12 of the flutes lacks a side-cutting edge. This produces a truly self-directional stability capacity. The dulling, relieving, or beveling of the leading edge of the flutes of the drill bit, as provided by the drill bit of the invention, do not cause the drill bit to change the drill behavior or direction, since the leading edge of the flutes at segment 12 (of FIG. 1) do not possess a side-cutting capacity as does the initial portion 11 (of FIG. 1) of the flutes. At the same time, because the flutes of segment 12 of FIG. 1, maintain the same diameter of the drill bit, the drill bit of the invention affords a drilling direction guidance capacity. The flutes of the drill bit maintain the ability to remove from the hole being drilled any chips and filings as they are formed. It is thus seen that the improved drill bit of the invention, having a non-side-cutting region at the upper portion of the drill bit flutes (shown by portion 12 of FIG. 1), provide drill guidance only and in effect protect the side walls of the bored hole from being inadvertently shaved (thus widening the hole), as almost invariably occurs in hand-held drilling operations.

The length of the sharp section (segment 11 of FIG. 1) of the leading edge of each flute of the drill may be of the order of 5 to 10 percent of the total length of the flute of the drill bit. The orientation and the depth of the beveled leading or side-cutting edge, that is provided by removal of the sharp cutting edge on the leading flute edge, is illustrated by broken lines 25 of FIG. 4, and may be formed such that a plane of the part of the bevel plane line 25 of FIG. 4 has a perpendicular relationship to a line 22 which extends from the center of the drill to the original leading edge of a given flute with a beveled depth equivalent to, for example, 5 percent of the diameter of the drill.

While the drill bit of the invention has particular advantage and utility with hand held drill bit rotating devices, the drill bit can also be used in stationery drill rotating devices such as a drill press. The improved drill bit of the invention substantially improves the precision of hand drilled holes, especially for technique sensitive drilling operations such as bone surgery. This novel result is directly attributable to the drill bit configuration of the invention and results from the beveling of the leading or side-cutting edge of the flutes of the drill except for an initial, specified length of the flutes of the drill bit wherein the leading edge portion of the flutes retain their sharpness and side-cutting capacity.

What is claimed is:

1. A fluted drill bit comprising:
   first and second ends;
   a shank portion located at said first end;
   a constant diameter fluted portion having at least one flute, connected to said shank portion, said fluted portion including a hole cutting portion and a guiding portion;

said hole cutting portion located at said second end and including at least one radial cutting edge, said at least one flute in said cutting portion including a sharp, side-cutting leading edge connected to said at least one radial cutting edge; and said guiding portion located between said cutting portion and said shank portion, said at least one flute in said guiding portion having a non-side-cutting leading edge, wherein said guiding portion comprises a majority of said constant diameter fluted portion.

2. The fluted drill bit of claim 1 wherein said hole cutting portion has a length of about 1/10 to 1/20 of said constant diameter fluted portion.

3. The fluted drill bit of claim 1 wherein the drill bit comprises two flutes.

4. The fluted drill bit of claim 1 wherein the drill bit comprises 3 flutes.

* * * * *